US00PP29434P2

(12) United States Plant Patent
Trees

(10) Patent No.: US PP29,434 P2
(45) Date of Patent: Jun. 26, 2018

(54) ***MIMULUS* PLANT NAMED 'BALBURANIM'**

(50) Latin Name: *Mimulus aurantiacus*
Varietal Denomination: Balburanim

(71) Applicant: The Conard-Pyle Company, West Grove, PA (US)

(72) Inventor: Scott C. Trees, Arroyo Grande, CA (US)

(73) Assignee: The Conard-Pyle Company, West Grove, PA (US)

( * ) Notice: Subject to any disclaimer, the term of this patent is extended or adjusted under 35 U.S.C. 154(b) by 0 days. days.

(21) Appl. No.: 15/530,787

(22) Filed: Feb. 28, 2017

(51) Int. Cl.
*A01H 5/02* (2018.01)

(52) U.S. Cl.
USPC ..... Plt./454
CPC ..... *A01H 5/02* (2013.01)

(58) Field of Classification Search
USPC ..... Plt./454
CPC ..... A01H 5/02
See application file for complete search history.

(56) References Cited

PUBLICATIONS https://issuu.com/starrosesandplants/docs/srp_catalog_2017_allpages/17; May 16, 2016, 2 pages.*

* cited by examiner

*Primary Examiner* — Kent L Bell
(74) *Attorney, Agent, or Firm* — Audrey Charles

(57) ABSTRACT

A new and distinct cultivar of *Mimulus* plant named 'Balburanim', characterized by its medium orange-colored flowers, medium green-colored foliage, moderately vigorous, compact-upright growth habit, is disclosed.

1 Drawing Sheet

Latin name of genus and species of plant claimed: *Mimulus aurantiacus*.

Variety denomination: 'Balburanim'.

BACKGROUND OF THE INVENTION

The present invention relates to a new and distinct cultivar of *Mimulus* plant botanically known as *Mimulus aurantiacus* and hereinafter referred to by the cultivar name 'Balburanim'.

The new cultivar originated in a controlled breeding program in Guadalupe, Calif. during August 2012. The objective of the breeding program was the development of *Mimulus* cultivars with large flowers, attractive flower coloration, and a compact-upright growth habit.

The new *Mimulus* cultivar is the result of cross-pollination. The female (seed) parent of the new cultivar is the proprietary *Mimulus aurantiacus* breeding selection coded MIM-348, not patented, characterized by its red and dark red bicolored flowers, medium green-colored foliage, and moderately vigorous, upright growth habit. The male (pollen) parent of the new cultivar is the proprietary *Mimulus aurantiacus* breeding selection coded 10797-A, not patented, characterized by its light blush peach-colored flowers, dark green-colored foliage, and vigorous, semi-upright growth habit. The new cultivar was discovered and selected as a single flowering plant within the progeny of the above stated cross-pollination during March 2013 in a controlled environment in Guadalupe, Calif.

Asexual reproduction of the new cultivar by terminal stem cuttings since March 2013 in Guadalupe, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balburanim' as a new and distinct cultivar of *Mimulus* plant:

1. Medium orange-colored flowers;
2. Medium green-colored foliage; and
3. Moderately vigorous, compact-upright growth habit.

Plants of the new cultivar differ from plants of the female parent primarily in flower color. Plants of the new cultivar differ from plants of the male parent primarily in flower color and growth habit.

Of the many commercially available *Mimulus* cultivars, the most similar in comparison to the new cultivar is 'Jelly Bean Orange', not patented. However, in side-by-side comparison, plants of the new cultivar differ from plants of 'Jelly Bean Orange' in at least the following characteristics:

1. Plants of the new cultivar are more compact than plants of 'Jelly Bean Orange'; and
2. Plants of the new cultivar have a larger corolla than plants of 'Jelly Bean Orange'.

In addition, the new cultivar is similar to BURST Orange 'Bosburan', U.S. Plant patent application Ser. No. 13/986,618, now abandoned. However, in comparison, plants of the new cultivar differ from plants of 'Bosburan' in at least the following characteristics:

1. Plants of the new cultivar have a flower color slightly different from plants of 'Bosburan'; and 2. Plants of the new cultivar have shorter pistils than plants of 'Bosburan'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balburanim'. The plant was grown as one gallon stock pot in an outdoor nursery in Guadalupe, Calif. In early December 2016, the plant was transferred to a greenhouse in West Grove, Pa. and held under greenhouse conditions.

DETAILED BOTANICAL DESCRIPTION

Figure 1:
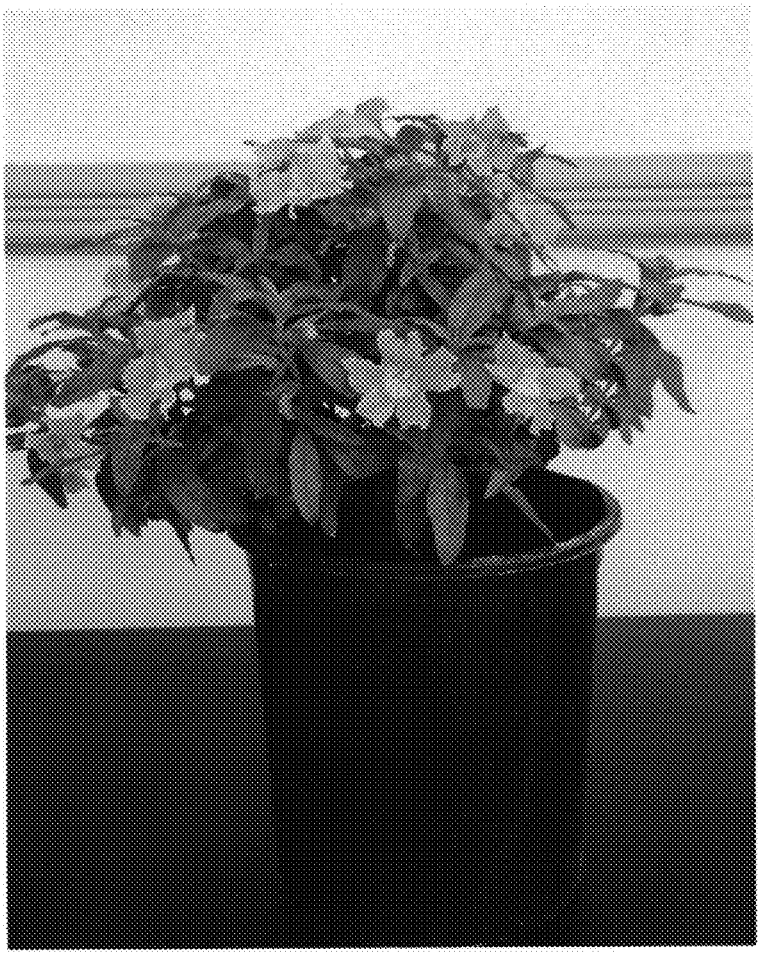
FIG. 1 illustrates a side view of the overall growth and flowering habit of 'Balburanim'.
Figure 2:
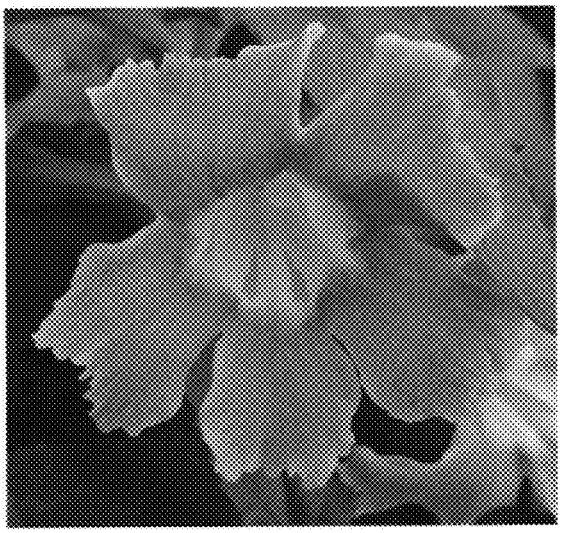
FIG. 2 illustrates a close-up view of an individual flower of 'Balburanim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2017 under natural light conditions in West Grove, Pa.

The following descriptions and measurements describe plants produced from cuttings from stock plants. The plants were grown in 1-gallon containers utilizing a soilless growth medium for 9 months in an outdoor nursery in Guadalupe, Calif. In early December 2016, the plants were transferred to West Grove, Pa. and held under greenhouse conditions to flower. Greenhouse temperatures were maintained at 74° F. to 80° F. (23° C. to 27° C.) during the day and approximately 66° F. to 70° F. (19° C. to 21° C.) during the night. Greenhouse light levels of 2,100 footcandles to 4,122 footcandles were maintained during the day. Measurements and numerical values represent averages of typical plants.

Botanical classification: *Mimulus aurantiacus* cultivar Balburanim.

Parentage:

*Female parent*.—Proprietary *Mimulus aurantiacus* breeding selection coded MIM-348, not patented.

*Male parent*.—Proprietary *Mimulus aurantiacus* breeding selection coded 10797-A, not patented.

Propagation:

*Type cutting*.—Terminal stem.

*Time to initiate roots*.—Approximately 10 to 14 days.

*Time to produce a rooted cutting*.—Approximately 21 to 25 days.

*Root description*.—Fibrous.

*Rooting habit*.—Freely branching.

Plant description:

*Commercial crop time*.—Approximately 10 to 12 weeks from a rooted cutting to finish in a 10 cm pot.

*Growth habit and general appearance*.—Moderately vigorous, compact-upright growth habit.

*Size*.—Height from soil level to top of plant plane: Approximately 30.0 cm. Width: Approximately 30.0 cm.

*Branching habit*.—Freely branching, pinching enhances basal branching. Quantity of main branches per plant: Approximately 4.

*Branch*.—Strength: Strong, somewhat flexible, becomes woody with age. Length: Approximately 12.0 cm. Diameter: Approximately 3.0 mm. Length of central internode: Approximately 3.0 cm. Texture: Viscid, densely glandular pubescent. Color of young stems: 145B. Color of mature stems: 199B.

Foliage description:

*General description*.—Quantity of leaves per main branch: Approximately 10. Fragrance: Slight. Form: Simple. Arrangement: Opposite.

*Leaves*.—Aspect: Perpendicular to stem, slightly reflexed. Shape: Elliptic. Margin: Serrate. Apex: Rounded acute. Base: Attenuate. Venation pattern: Pinnate. Length of mature leaf: Approximately 5.5 cm. Width of mature leaf: Approximately 1.3 cm. Texture of upper surface: Glabrous, glossy. Texture of lower surface: Glabrous, viscid, densely glandular pubescent. Color of upper surface of young and mature foliage: 137A with indistinguishable venation. Color of lower surface of young and mature foliage: Closest to 138B with midvein of 147C.

*Petiole*.—Length: Approximately 3.0 mm. Diameter: Approximately 3.0 mm. Texture: Glabrous, viscid, densely glandular pubescent. Color: 144D.

Flowering description:

*Flowering habit*.—'Balburanim' is freely flowering under outdoor growing conditions with substantially continuous blooming from spring through autumn and year-round in greenhouse environment.

*Lastingness of individual flower on the plant*.—Approximately 2 weeks.

Flower description:

*General description*.—Type: Single, salverform, zygomorphic, axillary, facing outward. Quantity per plant: Approximately 23. Fragrance: None detected.

*Bud*.—Rate of opening: Generally takes 2 to 3 days for bud to progress from first color to fully open flower. Quantity per plant: Approximately 6.

*Bud just before opening*.—Shape: Elongate. Length: Approximately 3.0 cm. Diameter: Approximately 1.0 cm. Texture: Glabrous, slightly viscid, glandular pubescent. Color: Sepals of 144B with folded midvein area of 137D, lobes of 163B.

*Corolla*.—Vertical axis: Approximately 4.5 cm. Horizontal axis: Approximately 4.0 cm.

*Lobes*.—Quantity: 5, fused to form a tube. Shape: Fan-shaped, upper two lobes reflexed. Margin: Irregularly sinuate and ruffled. Apex: Obtuse to truncate. Length from tube of upper two lobes: Approximately 2.1 cm. Length from tube of lower lobes: Approximately 2.0 cm. Width of upper two lobes: Approximately 2.1 cm. Width of lower lobes: Approximately 3.5 cm. Texture of upper and lower surfaces: Glabrous. Color of upper surface when first open: N163A and N163B with a thin margin of 8A. Color of lower surface when first and fully open: Between 167A and 167B. Color of upper surface when fully open: Between 167B and 167C with streaks of 172B and a thin margin of 8B.

*Corolla tube*.—Length: Approximately 4.0 cm. Diameter at distal end: Approximately 1.2 cm. Diameter at proximal end: Approximately 2.0 mm. Texture of inner and outer surfaces: Glabrous. Color of inner surface: 19D with two nectar glides at base of lower lobe of 21A. Color of outer surface: 23D.

*Sepals*.—Quantity per flower: 5, fused. Shape: Elliptic, folded at midveins. Margin: Entire. Apex: Acute. Length: Approximately 2.7 cm with one upper sepal of approximately 3.0 cm. Width: Approximately 4.0 mm. Texture of upper and lower surfaces: Glabrous, slightly viscid, glandular pubescent. Color of upper and lower surfaces: 144B with folded midvein area of 137D.

*Peduncle*.—Strength: Strong, flexible. Aspect: Acute angle to stem. Length: Approximately 5.0 mm. Diameter: Approximately 2.0 mm. Texture: Densely glandular pubescent. Color: 144B.

*Reproductive organs*.—Androecium: Stamen quantity: 4, didynamous, basifixed. Stamen length of longer pair: Approximately 2.0 cm. Stamen length of shorter pair: Approximately 1.5 cm. Filament length of fixed portion: Approximately 1.7 cm. Filament color: 1C. Anther shape: Bilobed, ovoid. Anther length: Approximately 3.0 mm. Anther color: 24B. Pollen amount: Moderate. Pollen color: 4B. Gynoecium: Pistil quantity: 1 per flower. Pistil length: Approximately 1.8 cm. Stigma shape: Flattened, bilobed. Stigma length: Approximately 1.0 mm. Stigma color: 160B. Style length: Approximately 1.8 cm. Style color: 160C. Ovary length: Approximately 5.0 mm. Ovary color: 144A.

Seed and fruit production: Neither seed nor fruit production has been observed.

Disease and pest resistance: Resistance to pathogens and pests common to *Mimulus* has not been observed.

What is claimed is:

1. A new and distinct cultivar of *Mimulus* plant named 'Balburanim', substantially as herein illustrated and described.

* * * * *